United States Patent [19]
Lefevre et al.

[11] Patent Number: 5,730,941
[45] Date of Patent: Mar. 24, 1998

[54] DEVICE FOR THE OPTICAL INSPECTION OF A FLUID, ESPECIALLY FOR HEMATOLOGICAL ANALYSES

[75] Inventors: Didier Lefevre, Saint Clement De Riviere; Bernard Kress, Strasbourg, both of France

[73] Assignee: A B X, Montpellier, France

[21] Appl. No.: 653,325

[22] Filed: May 24, 1996

[30] Foreign Application Priority Data

May 24, 1995 [FR] France ................................ 95 06228
Nov. 27, 1995 [FR] France ................................ 95 14033

[51] Int. Cl.$^6$ .................................................. G01N 21/64
[52] U.S. Cl. ................... 422/73; 422/82.05; 422/82.08; 356/73
[58] Field of Search ........................... 422/82.05, 82.08, 422/82.09, 73; 436/164, 172, 63; 356/72, 73, 336, 338

[56] References Cited

U.S. PATENT DOCUMENTS

| | | | |
|---|---|---|---|
| 3,754,814 | 8/1973 | Leith | 350/162 R |
| 4,348,107 | 9/1982 | Leif | 356/72 |
| 4,690,561 | 9/1987 | Ito | 356/339 |
| 4,765,737 | 8/1988 | Harris et al. | 356/336 |
| 4,915,501 | 4/1990 | Steen | 356/343 |
| 5,027,359 | 6/1991 | Leger et al. | 372/18 |
| 5,029,975 | 7/1991 | Pease | 350/96.27 |
| 5,138,181 | 8/1992 | Lefevre et al. | 250/573 |
| 5,142,140 | 8/1992 | Yamazaki et al. | 250/222.2 |

FOREIGN PATENT DOCUMENTS

| | | |
|---|---|---|
| 0 424 934 | 5/1991 | European Pat. Off. |
| 0 425 381 | 5/1991 | European Pat. Off. |

OTHER PUBLICATIONS

Skupsky et al., "Speckle–Free Phase Plate (diffuser) for Far–Field Applications" Journal of Applied Physics, vol. 74, No. 7, (1993), 4310–4316.

*Primary Examiner*—Jeffrey Snay
*Attorney, Agent, or Firm*—Foley & Lardner

[57] ABSTRACT

It includes a measuring space (8) comprising a constrained passage (15) for the fluid, a monochromatic light source (31) delivering a beam (F1) to optical elements (6, 32, 34) including a first diffractive optical element (32) having a diffractive network (38) predetermined as a function, on the one hand, of the characteristics of the source and, on the other hand, of chosen geometrical and spectral characteristics for the illumination of the constrained passage, and suitable for inducing fluorescence of at least part of the fluid, and first (19–20), second (34–36) and third (40) optoelectronic elements intended to collect, respectively, a transmitted beam, fluorescence and a diffracted beam, and suitable for delivering to an analysis unit (24) signals relating to the contents of the beams. At least one of the beams emanates from a second diffractive optical element (42) having a second diffractive optical network which is predetermined as a function of a frequential and geometrical transfer function of at least one of the optoelectronic elements.

21 Claims, 5 Drawing Sheets

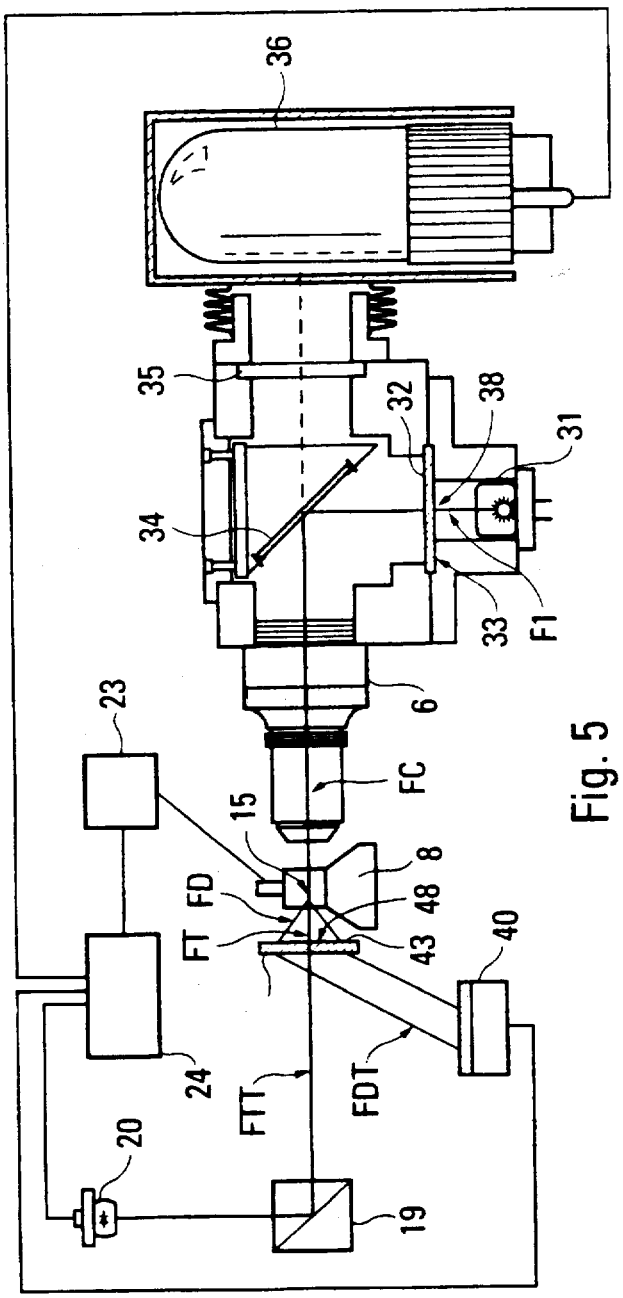
Fig. 5
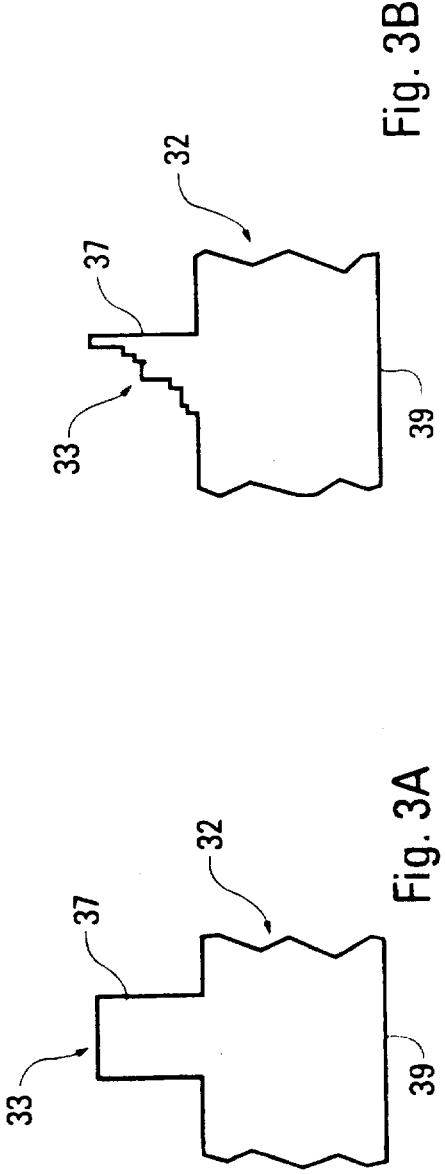
Fig. 3A
Fig. 3B

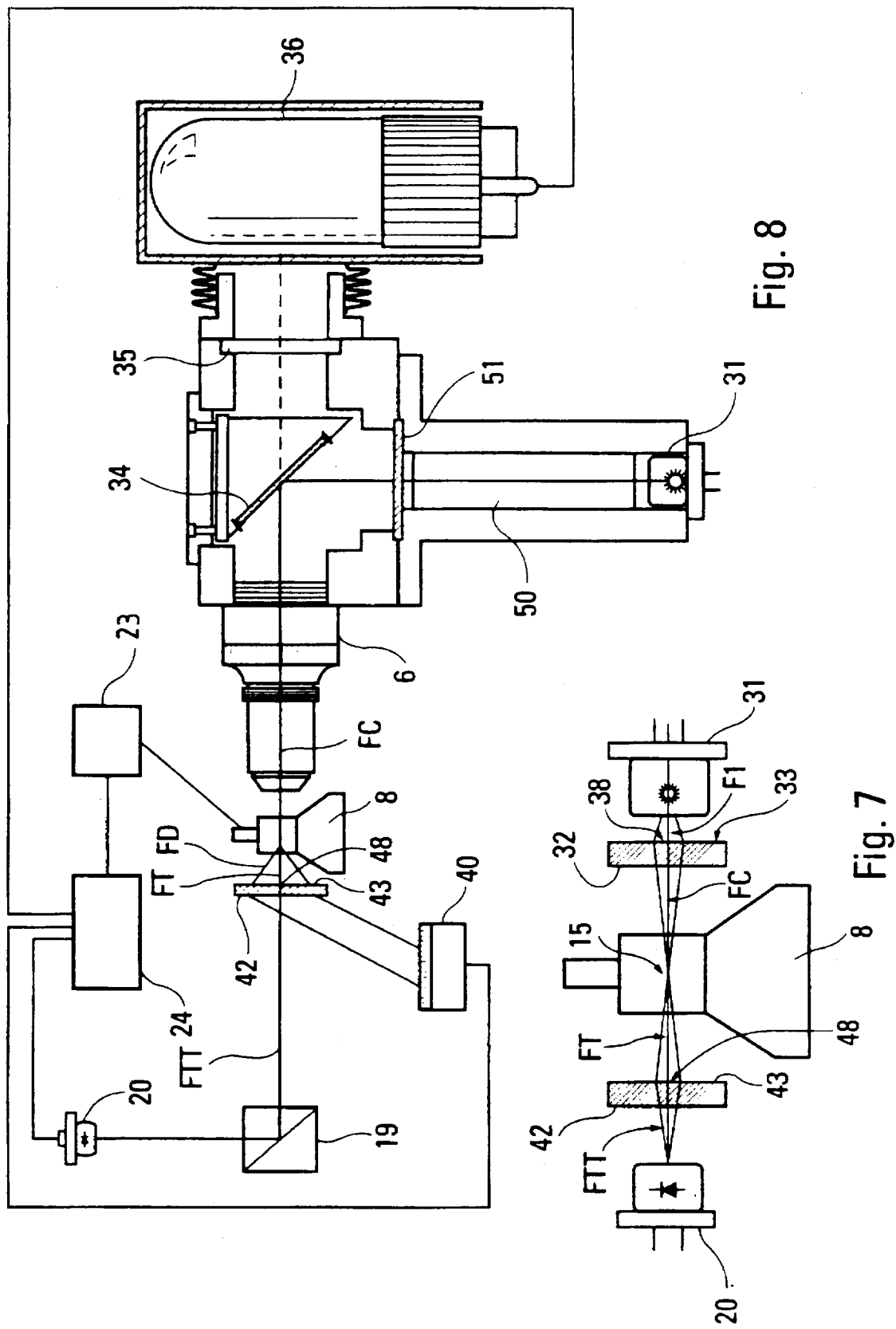

DEVICE FOR THE OPTICAL INSPECTION OF A FLUID, ESPECIALLY FOR HEMATOLOGICAL ANALYSES

The invention relates to the optical inspection of particles of a gaseous or liquid fluid, and more particularly to the shaping of light beams used in particulate counting appliances, especially in flux cytometry, hematology and medical diagnostics.

Certain of the current appliances automatically distinguish between particles of the fluid according to the family to which they belong and, in certain cases, the fact that they belong to subvarieties of a family. These distinctions necessitate either a number of different devices each capable of carrying out part of the desired analysis, or else a device equipped with a number of analysis zones (or chambers) arranged in series.

A device capable of carrying out part of this type of analysis is described in French Patent No. 89 14120 belonging to the Applicants. It includes a measuring space (or tank) comprising a constrained passage for the fluid, upstream optical means suitable for collecting the light emanating from a source and for delivering the said collected light at the level of the constrained passage in accordance with the geometrical and spectral characteristics chosen, and first sensor means suitable for delivering to an analysis unit signals ("first signals") which are representative of data ("first data") conveyed by a light having chosen geometrical and spectral characteristics and collected by first downstream optical means after passage through the constrained passage.

"Spectral characteristics" are understood to mean both the intensity and the wavelength of the source light or of the light obtained after interaction with the fluid at the level of the constrained passage, and "geometrical characteristics" are understood to mean the general shape and topology of the illuminated zone or of the measuring zone of the sensor concerned.

Moreover, "optical means" are understood to mean the optical system for collecting the light upstream or downstream of the constrained passage (for example a microscope objective), and "sensor means" are understood to mean electronic detection elements of the diode, photomultiplier or other similar sensor type.

One of the difficulties of these measuring operations lies in the fact that the particles of the fluid to be inspected, which pass through the constrained passage under illumination, must receive the same light intensity in the same time interval. In other words, the distribution of light over the entire surface defined by the constrained passage must be uniform. This necessitates a preliminary shaping of the beam which is delivered by the light source and intended to illuminate the said constrained passage.

Moreover, by reason of the geometrical and spectral characteristics of the light obtained after interaction between the fluid and the light beam emanating from the source, it is currently necessary to utilize numerous and bulky optical means.

To sum up, the current devices have a number of drawbacks, such as for example bulkiness, complexity, relatively major brackets of uncertainty which vitiate the results of the measuring operations, or the impossibility of differentiating between the subvarieties of a given family. These drawbacks will be dealt with again later on and in detail.

One object of the invention is therefore to obtain a device for the optical inspection of particles of a fluid, of the type initially described, which does not have the drawbacks of the devices belonging to the prior art, especially in terms of output, bulkiness, complexity and cost.

According to the invention, at least one of the upstream optical means and of the first downstream optical means includes at least one first diffractive optical element intended, according to its position in relation to the constrained passage, for the geometrical and/or spectral shaping, either of the light beam delivered by the source, or of the light obtained after interaction between the fluid and the source light.

This element possesses at least one surface which interacts with the light that it collects, and has a first predetermined three-dimensional motif which is suitable for carrying out a predetermined interaction between the light that it collects and the light that it delivers, taking into account the respective characteristics of these two lights.

"Diffractive optical element" is understood to mean a component of which at least one face has a motif producing a structure capable of causing the photons emitted by a source having known characteristics to interfere in a constructive manner, in accordance with the laws of diffractive optics.

In this way, the shaping may have a bearing on the beam upstream of the space for interaction between the fluid and the source light and/or downstream of the said space.

According to one aspect of the invention, the geometrical and spectral characteristics chosen, which are required for the illumination of the constrained passage, include uniform illumination, at the wavelength chosen, of a substantially plane, closed surface having a given geometry.

It has been observed that, by replacing at least part of the optical means intended, in the prior art, for shaping the light emitted by the source, by a single diffractive optical element having very low bulkiness and specifically adapted, on the one hand, to the source and, on the other hand, to the geometrical and spectral characteristics required for the illumination of the fluid to be analysed, it is possible to appreciably reduce the bulkiness of the device, and above all to very appreciably improve the precision and resolution of the measuring operations.

No conventional geometrical optical system of low bulkiness and moderate cost can make it possible to obtain an illumination verifying such characteristics.

In the same way, no conventional optical means of low bulkiness and moderate cost can make it possible to collect the light emanating from the interaction between the fluid and the source light with so much efficiency, while at the same time making possible geometrical and/or spectral filtering of this collected light.

According to another characteristic of the invention, the light source is a source with substantially monochromatic radiation, the emission wavelength of which is chosen in such a way that it induces fluorescence of at least part of the fluid passing through the constrained passage. Moreover, there are provided second sensor means which are intended to collect at least part of the fluorescence emitted by the fluid and to deliver, to the analysis unit, signals (second signals) which are representative of data (second data) conveyed by this collected fluorescence.

The fluid to be inspected is processed beforehand by a suitable cytochemical means consisting in specifically coloring certain subvarieties of the particles it contains by means of a fluorescent dye.

By replacing the source belonging to the prior art, which is of the lamp type, by a monochromatic source, such as a laser diode for example, it is possible to adapt the device to the fluid to be analysed, so that the wavelength emitted by the said source can give rise to fluorescence of the subvarieties colored.

A number of modes of embodiment of the device according to the invention may be envisaged. A first mode in which use is made of a single diffractive optical element upstream of the constrained passage for shaping the source light, the collection of the light emanating from the interaction between the fluid and the source light being carried out in the conventional manner by refractive optical means. A second mode in which use is made of one or a number of diffractive optical elements only to collect the light emanating from the interaction between the fluid and the source light, the shaping of the source light being carried out in the conventional manner by refractive optical means. A third mode in which use is made of a diffractive optical element upstream of the constrained passage for shaping the source light, and of one or a number of diffractive optical elements for collecting the light emanating from the interaction between the fluid and the source light.

In the first mode of embodiment, the cooperation of the monochromatic source with a diffractive optical element, which is located upstream of the constrained passage and designed to work with this particular source, appreciably reinforces the quality of the illumination, from the point of view of definition of the surface illuminated and, above all, of uniformity of the intensity of illumination over the whole of the area of the said surface.

In the second form of embodiment, the device may integrate a plurality of different and non-destructive analyses techniques, and especially techniques involving analysis of fluorescence, analysis by transmission and analysis of diffraction at different angles, in a more restricted volume than in the devices belonging to the prior art. Furthermore, these analyses can be carried out at the same time and with a single sample.

It is also possible to envisage separation between a number of wavelengths contained in an input beam in order to form a number of non-collinear monochromatic beams, and to focus each beam at a predetermined, given place with a particular geometry. But spectral and/or geometrical filtering may also be carried out.

In the third form of embodiment, it is henceforth possible to gain freedom from all or some of the traditional optical elements of the microscope objective or convergent lens type.

It is very advantageous if the first and second three-dimensional motifs are first and second diffractive networks engraved in transparent substrates at the source light wavelength and/or the fluorescence wavelength.

The production of the diffractive networks by classic holography, by coagulating fringes of interferences in a photosensitive emulsion, might be envisaged. But networks of this kind do not always have the temporal stability desired and the industrial manufacture thereof is more difficult than that of an engraved diffractive network.

Engraved diffractive networks of this kind may be produced by microlithography, for example by electron beam or laser ablation. The substrate may be chosen as a function of the emission wavelength and fluorescence wavelength in such a way that it is as unabsorbent as possible, thus making it possible to reinforce the efficiency of diffraction of the diffractive optical element.

According to another aspect of the invention, the first and second diffractive networks are of the digital type with relief modulation, the said modulation representing a predetermined function capable of coherent diffracting action on the phase and/or amplitude, respectively, of the light emitted by the source and of the light obtained after passage through the constrained passage.

Each function is determined with the aid of a computer, taking into account the characteristics of the light to be collected (source, or transmitted beam and fluorescence) and of the surface to be illuminated (fluid, or detection surface of the detector or detectors), and then transformed digitally into basic elements which form a diffractive network. Each element possesses a given position and a given height, which justifies the designation "diffractive network with relief modulation".

According to another characteristic of the invention, each diffractive network possesses relief modulation of at least two levels, and preferably sixteen levels.

Since modulation is carried out digitally, the height of each element is coded in binary manner. It is therefore possible to associate one level with each height. The number of levels of modulation therefore varies according to powers of 2. In principle, therefore, this number can only assume the values 2, 4, 8, 16 . . . .

The efficiency of diffraction of each network is going to depend upon the degree of similarity between the calculated diffracting function and the engraved three-dimensional motif. This degree of similarity depends, for its part, upon the pitch between two consecutive levels, or in other words, upon the number of levels defining the maximum amplitude of the diffracting function.

The higher the number of levels, the greater is the efficiency of diffraction. But it can be demonstrated that this efficiency increases rapidly up to about 95%, when the maximum intensity of the function is converted into 16 levels, then it tends very slowly towards an asymptote corresponding to 100% efficiency. However, the costs of manufacturing a network with relief modulation increase in a substantially exponential manner with the number of levels. Consequently, modulation at more than 16 levels would entail very high additional costs for a very small gain in efficiency.

The diffractive optical elements may be of the so-called "Fourier" type or of the so-called "Fresnel" type. Naturally, one may be of the Fresnel type while the other (or another) is of the Fourier type, or conversely.

"Fourier optical system" is understood to mean an element that delivers a beam of waves, the +1 and −1 orders of which are real, which allows two variants. A first, so-called "centred" (or in English "on axis") variant, in which the two orders +1 and −1 overlap on the optical axis of the element. A second, so-called "de-centred" (or in English "off axis") variant, in which the two orders +1 and −1 are distributed symmetrically on both sides of the optical axis of the element, without overlapping. The second variant makes it possible, of course, to obtain a more suitable mode since, by selecting one of the off-axis orders +1 or −1, freedom is gained from the residual central order 0, but that divides the diffraction output by two since the energy supplied by each order is no longer added up. This type of element delivers an image of the object in a distant field, which means that the image of the object is distinct at infinity.

"Fresnel optical system" is understood to mean an element that delivers a beam of waves, of which the +1 order is real and the −1 order is virtual, which allows only one possibility. An optical system of this kind is therefore equivalent to a lens in conventional geometrical optics. This type of element delivers an image of the object in a near field.

The diffractive optical element responsible for shaping the beam upstream of the constrained passage preferentially includes a single surface comprising a Fresnel-type diffracting motif with sixteen levels.

This solution is currently preferred since, as indicated above, the Fresnel optical system delivers an image of the object in a near field. Consequently, the diffractive element on its own is capable, at the same time, of carrying out a uniform distribution of the energy contained in the incident beam, and of focusing this energy in a given place, such as at the front-lens of an objective for example, or directly at the level of the constrained passage, without its being necessary to interpose a focusing lens, such as is the case for Fourier optical systems. That therefore makes it possible to reduce, a little further still, the bulkiness of the inspection device.

Also in a preferential manner, the diffractive optical element responsible for shaping the light downstream of the constrained passage includes a single surface comprising a diffracting motif of the Fourier type with sixteen levels.

This solution is currently preferred since, as indicated above, the Fourier optical system delivers an image of the object in a distant field and is able to function in centred mode, thus making it possible to deliver the distinct image of the transmitted beam and/or of the fluorescence onto a relatively remote detection surface, without recourse to other optical elements, and to lose a minimum of light signal.

In the description that follows, which is given by way of an example, reference is made to the appended drawings, in which:

FIGS. 3A and 3B illustrate, respectively, part of a diffractive optical element, viewed in transverse section, for modulation at two levels (A) and at 16 levels (B);

FIG. 5 is a diagram illustrating a device according to the invention in a second mode of embodiment;

FIG. 7 is a diagram illustrating a partial and simplified variant of the device in FIG. 5; and FIG. 8 is a diagram illustrating a device according to the invention in a third mode of embodiment.

The appended drawings comprise numerous elements of a certain character, which it is difficult to define completely by means of the text. They consequently form, on these grounds, an integral part of the description and may contribute to the definition of the invention.

Figure 1:
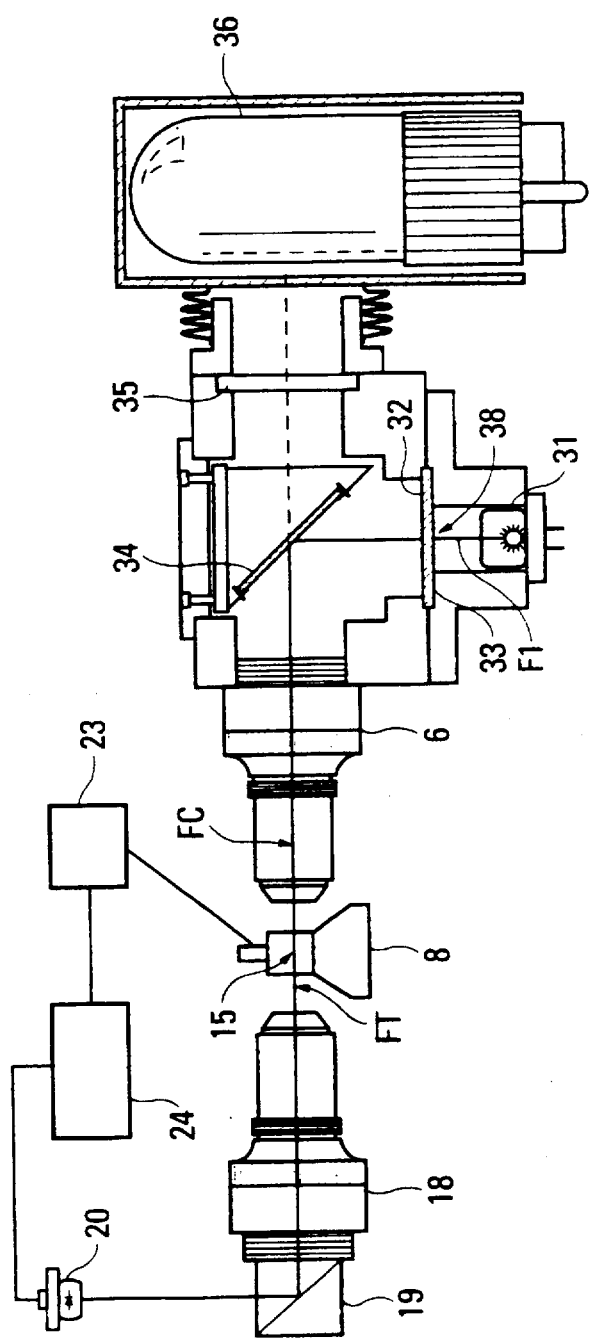
FIG. 1 is a diagram illustrating a device according to the invention in a first mode of embodiment.
Figure 2:
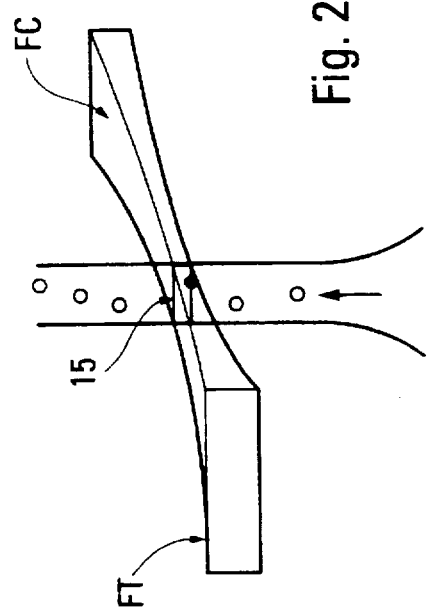
FIG. 2 is an enlargement of a central part of the zone of interaction between the calibrated analysis beam and the fluid, in the device in FIG. 1.

Reference will be made, first of all, to FIGS. 1 and 2 in order to describe a first mode of embodiment of the device according to the invention.

The device includes a monochromatic light source which has a very low electrical power consumption and the emission wavelength of which is chosen as a function of the spectral band of excitation of the fluorescent dye chosen for coloring certain subvarieties of particles of the fluid to be analysed.

This source is preferably a laser diode, but it may be a laser or, more generally, a source, the wavelength and emission power of which allow fluorescence of colored subvarieties which are to be analysed.

The laser diode 31 delivers a beam F1, which has a substantially elliptical cross-section and the energy of which has a Gaussian distribution, in the direction of a diffractive optical element 32, which will be dealt with again later on. This element 32 has a front surface 33, opposite the active diode, which acts upon the beam F1 delivered by the said diode 31 in such a way that it has chosen geometrical and spectral characteristics at the level of a constrained passage 15 in the measuring space 8 which, in this case, is a tank. The beam processed by the diffractive optical element 32 is referred to as "FC".

The geometrical characteristics have a bearing on the shape of the beam FC and on its dimensions in the constrained passage 15, which dimensions must be substantially equal to the transverse dimensions of the flux. In the example described, the beam possesses a rectangular shape having dimensions, for example, of 100 μm×30 μm. Naturally in other applications, or else if the measuring space is not a tank, the shape of the beam FC at the level of the constrained passage may be different from a rectangle. The same applies to the dimensions. Almost all shapes of beam may be envisaged since the diffractive element is produced as a function of the characteristics of the source and of the characteristics which the beam must have at the level of the constrained passage 15 in the measuring space 8.

Moreover, the spectral characteristics have a bearing on the energy distribution at the level of the constrained passage, which distribution must be virtually uniform (preferably with deviations lower than 5%) over the whole of the rectangle described above, and on the monochromaticity of the beam, which is ensured directly by the source.

In the mode of embodiment illustrated, the diffractive element 32 in fact delivers a beam FC having a uniform and rectangular energy distribution, but having dimensions greater than those previously described, at the level of the front-lens of a first microscope objective 6 (×20) which reduces the dimensions of the rectangular beam in such a way that they are equal to those required at the level of the constrained passage 15 (in this case, 100 μm×30 μm). There is therefore cooperation between the diffractive element and the first objective 6 in order to deliver the beam FC at the level of the measuring chamber 16. But it is clear that it is possible to dispense with such cooperation, the diffractive element being then designed to deliver the beam having chosen characteristics directly at the level of the constrained passage in the tank 8.

Furthermore, in the example illustrated, the beam F1 emanating from the diode 31 is oriented perpendicularly to the optical axis of analysis. Consequently, in order to reach the first objective 6, the beam F1 undergoes 90° reflection on a dichroic lamina 34 centred on the optical axis of analysis.

Beyond the first objective, the beam FC passes through the constrained passage 15 in the measuring tank 8. It is then transformed into a transmitted beam FT by interaction with the fluid, then enters a second microscope objective 18 (×20) which is identical to the first one 8 and which shapes it and directs it towards a separator cube 19 which reflects it perpendicularly towards a collecting photodiode 20. This photodiode is located at a distance from the constrained passage 15 equal to that which separates the diffractive element 32 from this same constrained passage. Thus, the dimensions of the transmitted beam FT at the level of the photodiode 20 are substantially equal to those which the beam has on passing out of the diffractive element 32. The second objective 18, the separator cube 19 and the photodiode 20 form first optoelectronic means.

The photodiode 20 measures the intensity of the transmitted beam FT which is more or less absorbed by the different subvarieties of particles in the fluid, with which it interacts. This fluctuation in absorbency, which makes it possible to differentiate between the subvarieties of particles, is due not only to their different volumes, but also to their internal peculiarities. This measurement is transformed into signals which are sent to an analysis unit 24, where they are, if necessary, correlated with other signals emanating from another channel 23 with a view to counting the subvarieties of particles. This last technique, and also others which make it possible to carry out measurements by resistivity and by transmission are thoroughly known to the person skilled in the art and are related in detail in the aforesaid French patent.

It is also possible to provide a channel for adjusting the objectives substantially in the axis of the transmitted beam FT. It includes a focusing screen 21 which makes it possible to form the superimposed image of the beam FC at the level of the constrained passage 15 and of the fluid, and a divergent lens 22 interposed between the focusing screen 21 and the separator cube 19 intended to enlarge the aforesaid superimposed image.

The device proposed also includes second optoelectronic means (optical means and sensors) for collecting other data in the measuring tank.

In actual fact, the emission wavelength of the laser diode 31 is chosen in order to induce fluorescence of certain subvarieties of particles which are contained in the fluid to be analysed and are colored beforehand by a suitable fluorescent dye. When subjected to a given incident light radiation, the dye contained in the colored particles absorbs this radiation and re-emits, virtually instantaneously ($10^{-8}$ sec.) and in an isotropic manner, radiation with a wavelength greater than the incident radiation. This re-emission is called "fluorescence". It is therefore possible to recover part of the fluorescence, either at 90° from the optical axis of analysis or parallel to the said axis (epifluorescence). The device in FIG. 1 illustrates a measurement of epifluorescence at 0° (fluorescence picked up parallel to the optical axis in the opposite direction to the beam F1 emanating from the diode 31).

The fluorescence to be collected passes through the first objective 6, then the dichroic lamina 34, and is directed towards an interferential filter 35 which selects the only fluorescence wavelength of the fluorescent particles, which makes it possible to reject all the other stray wavelengths, such as that of the laser diode for example. Then, once it has been filtered, the fluorescence is collected by a photomultiplier tube 36 connected to the analysis unit 24. The intensity measured by the tube 36, over a given time interval, is correlated with the other measurements by transmission and by resistivity, which make it possible to deduce therefrom data on certain subvarieties of particles, and especially on their respective numbers.

It is clear that the respective positionings of the photomultiplier tube and of the laser diode coupled to the diffractive element can be completely inverted. In the same way, the device according to the invention can be produced by accommodating the laser diode, coupled to the diffractive element, parallel with the optical axis of analysis, and by locating the second optoelectronic means for collecting the fluorescence (photomultiplier tube and interferential filter) opposite the measuring space 8 so as to collect the fluorescence at 90° from this optical axis of analysis.

The diffractive optical element 32 (see FIGS. 3A, 3B and 4) includes, on its front face 33, opposite the laser diode 31, a three-dimensional motif which is formed by the juxtaposition of substantially square basic elements 37 and is of variable height. This juxtaposition forms a diffractive network 38 with relief modulation. The height of each basic element is obtained by digitising a function capable of coherent diffracting action on the phase and/or the amplitude of the light emitted by the source.

Calculation of the diffracting function may be carried out by establishments such as the Photonic Systems Laboratory of the Ecole Nationale Supérieure de Physique [National College of Physics] in Strasbourg, which likewise proceeds with digitisation of this function in such a way that it is possible to guide the machine intended to produce the diffracting motif corresponding to the said function.

This calculation is carried out with the aid of a software package for the computer-aided design of optical systems. When the characteristics of the waves of the beam F1 delivered by the laser diode 31, and the characteristics which the waves of the beam must have at the level of the front-lens of the objective 6 are known, it is possible, by likening the diffractive optical element 32 to a transfer matrix and by using an iterative calculation algorithm capable of solving Maxwell's equations, to calculate a diffracting function capable of transforming the beam emanating from the diode into an analysis beam. Naturally, although the algorithm is iterative, it may be necessary to carry out successive approximations in order to determine a diffracting function.

A number of algorithms may be used for the calculation, such as for example those known under the following names: "simulated annealing algorithm", "Gerchberg-Saxton algorithm in a near field", "algorithm for the diffusion of complex errors" or "genetics algorithm based on Darwin's theory of evolution".

These algorithms also take into account the characteristics of the substrate in which the diffractive element is produced, the technique for manufacturing the diffracting network on this element and the type of the said network (Fourier or Fresnel). The Fresnel network is preferable since, supplying images in a near field, it does not necessitate the use of a convergent lens.

Once the diffracting function has been calculated, it is necessary to digitise it so that it can be transformed into a computer file representative of a digital motif forming a diffractive network. This file is generally in the form of a 1024×1024-element matrix, with each element coding part of the motif.

For that purpose, a binary value (or a level) is associated with the value of the function at a given point. The encoding being binary, its precision therefore depends upon the pitch existing between two consecutive values. In order to obtain a very small pitch, it is necessary for the maximum amplitude of the function to correspond to the greatest possible number of levels.

Figure 4:
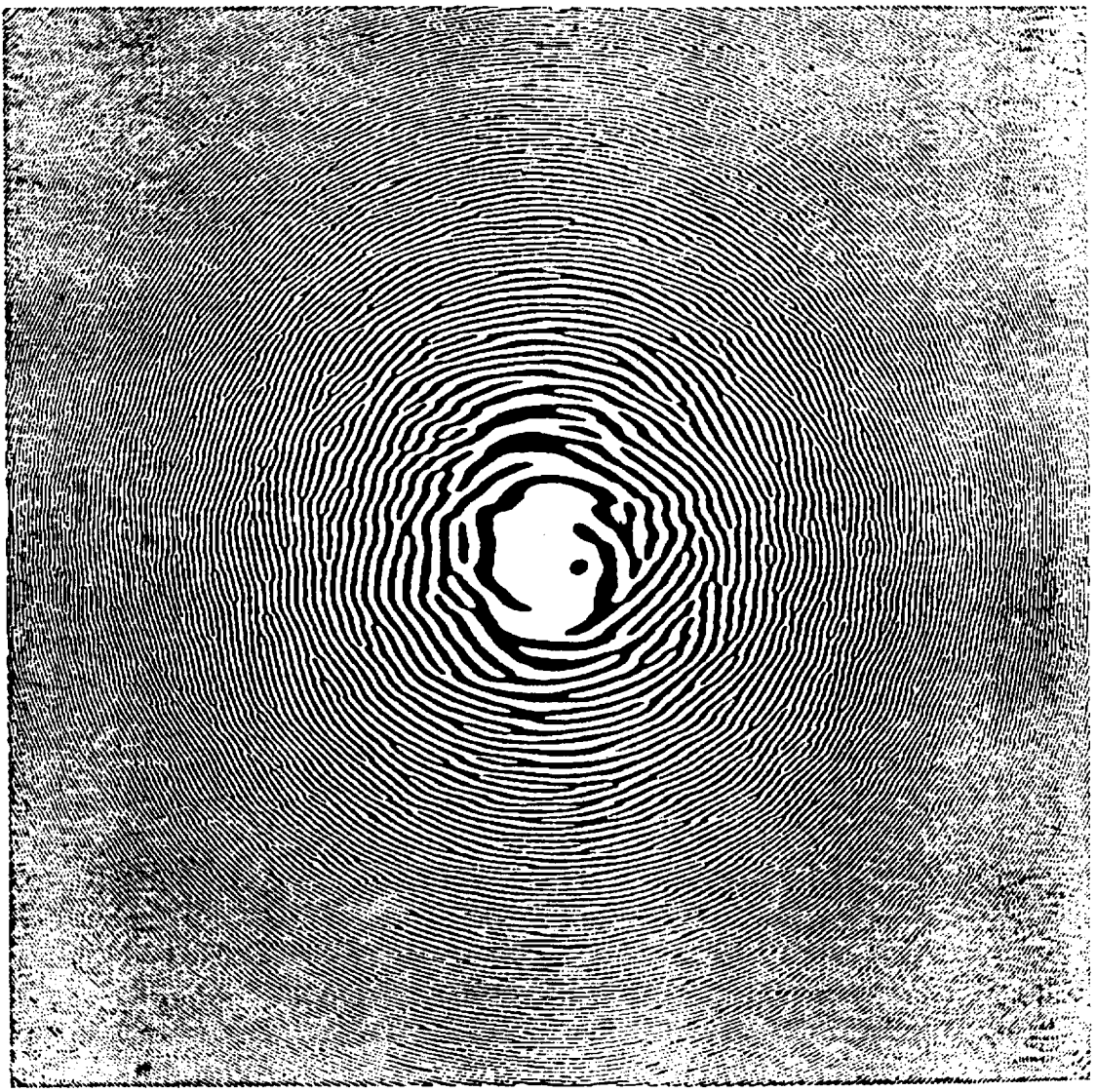
FIG. 4 is an example of an image of a diffractive network of the Fresnel type with two phase levels.

For material reasons, it is not possible to define exhaustively here, over 1024×1024 points, a diffractive network, for example of the Fresnel type with two phase levels. But in the absence of this, an image with two levels (black and white) from an example of such a diffractive network is illustrated in FIG. 4.

As explained in the introduction, beyond 16 levels, the diffraction output of the optical element rises very slowly, whereas the cost of manufacturing it increases very rapidly. Consequently, a diffractive optical element with 16 levels, which gives a diffraction output of around 95%, is sufficient to make it possible to obtain an analysis beam having homogeneity which is constant to within about 5%.

In FIGS. 3A and 3B, there can be seen a transverse section through a diffractive element 32 in which the basic elements 37 of its diffractive network 38 are binary (A) or have 16 levels (B), respectively.

Since the action of the diffractive element 32 is governed by the laws of diffraction, each basic element 37 has dimensions which are substantially equal to or lower than the emission wavelength of the diode 31. Consequently, in order to produce these basic elements, it is essential to use a technique, the resolution of which is of the order of about ten nanometers. Currently, the best technique is microlithography, and more particularly microlithography using a chromium mask with "binary grey levels".

The chromium mask is produced in the form of grey levels coded in a binary manner exactly like a grey graduated shading produced by a laser-type printer. This mask is deposited above a layer of resist which is itself deposited on a substrate. The mask is illuminated by an ultraviolet light which will give rise, under the effect of the different levels of the said mask, to the printing of the resist according to variable doses. The resist, which contains an image of the relief to be transferred, is then developed, which reveals the said relief. The relief on the developed resist is then transferred to the substrate by selective ionic reactive machining (better known in English under the acronym RIBE).

Each basic element 37 is thus engraved in a substrate 39, which is transparent at the emission wavelength of the laser diode 31. This substrate is produced in a material of the quartz or BK7 type.

Naturally, it is possible to provide numerous other types of substrate. In the same way, the methods of manufacture are not limited to the one described above. Any other method capable of producing a diffractive network of the type previously described may be envisaged. Thus, it will be possible to use an embossing technique, as is the case in the field of audio compact discs.

Reference will now be made to FIG. 5 in order to describe a preferential mode of embodiment of the invention, which includes all the elements of the device in FIG. 1 with the exception of the microscope objective 18, which is replaced by a second diffractive optical element 42 which receives, on its input face 43, the transmitted beam FT emanating from the tank 8, and transforms it into a processed transmitted beam FTT and a processed diffracted beam FDT.

The device therefore includes first optoelectronic means 19 and 20, which are installed downstream of the tank 8 and of the second diffractive optical element 42, in order to carry out analyses by transmission using the processed transmitted beam FTT, and also second optoelectronic means 34-36 in order to carry out analyses of fluorescence, the said second means being likewise installed upstream of the constrained passage 15 in order to collect the epifluorescence.

In this mode of embodiment there are also provided, downstream of the constrained passage 15 and of the second diffractive optical element 42, third optoelectronic means in order to carry out analyses of diffraction at different angles on the processed diffracted beam FDT. This analysis technique, which is well known to the person skilled in the art, makes it possible to obtain data on the surface state, morphology (shape) and content of certain particles, as a function of the angle of diffraction exhibited by the diffracted beam FD emanating from the interaction between the fluid and part of the light beam F1 emanating from the source.

These third optoelectronic means include a detector 40 which makes it possible to deliver to the analysis unit 24, to which it is connected, analogue signals (although these may also be digital ones) which are representative of data conveyed by the processed diffracted light FDT. The detector 40 includes, for example, one or a number of microchannel wafers, or a plurality of photoelectric microcells making it possible to precisely detect the planar coordinates of a diffracted photon that reaches it.

On receiving a signal emanating from the detector 40, the processing unit 24 is in a position to precisely deduce therefrom the angle of diffraction. This signal can be correlated with other signals emanating from other analysis channels (20, 36, 23) in order to deduce therefrom data on the subvariety of particle which has given rise to the said diffraction.

Figure 6:
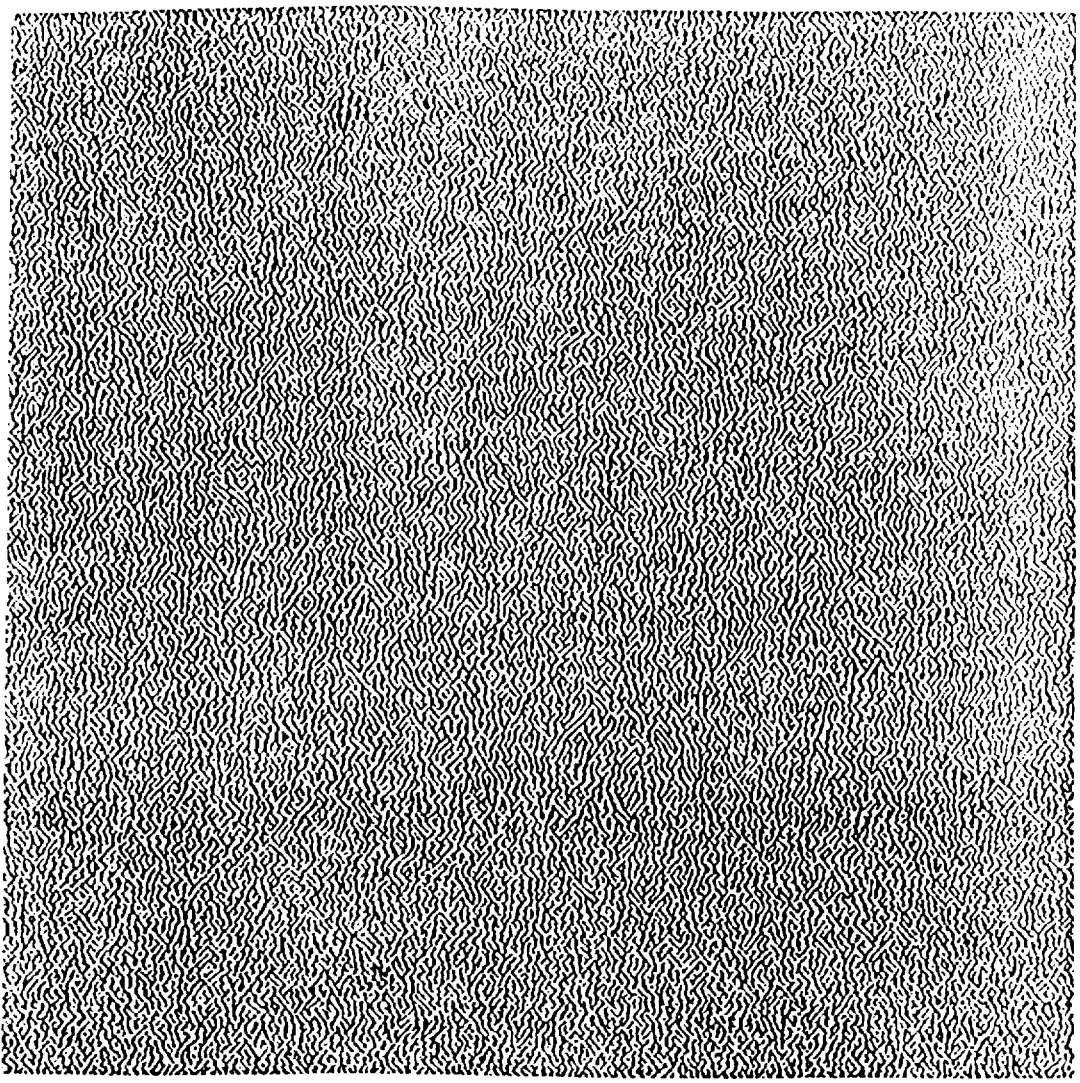
FIG. 6 is an example of an image of a diffractive network of the Fourier type with two phase levels.

Reference will now be made to FIGS. 3A, 3B and 6 in order to describe the second diffractive optical element 42, which may be produced in the same manner as the first diffractive optical element 32, for example by engraving. Only its three-dimensional diffractive motif, and therefore its diffractive network 38 with relief modulation, is totally different from the first. Consequently, these different parts bear the same references as those of the first element, but increased by 10.

Nevertheless, in a mode of embodiment which differs from the latter, in which the fluorescence would be picked up downstream of the tank (at 0°), its substrate may likewise not be identical to that of the first element, insofar as it must be transparent, not only at the wavelength of the light emitted by the source, but also at the fluorescence wavelength.

Its three-dimensional motif is formed by the juxtaposition of basic elements 47 which are substantially square and of variable height, the said juxtaposition forming the diffractive network 48 with relief modulation which is engraved on the front face 43, opposite the constrained passage 15.

The calculation of the three-dimensional motif is also carried out with the aid of the software for the computer-aided design of optical systems. The optical element is likened to a transfer function between the two inputs constituted by the transmitted and diffracted beams, FT and FD respectively, emanating from the tank 8, and the outputs constituted by the channels for analysis by transmission and by diffraction. In actual fact, the transfer function must provide focusing without loss of data, on the one hand, of the transmitted beam on the detection surface of the photodiode 20 and, on the other hand, of the diffracted beam on the detection surface of the detector 40, in such a way that a detection element on the said detector 40 corresponds to a given angle of diffraction at the output of the tank 8.

The parameters of this calculation are therefore, at the input, the wavelength (or frequency) of the source light, the geometry of the transmitted beam FT and the geometry of the diffracted beams FD and, at the output, the geometry of the processed transmitted beam FTT at the level of the detection surface of the diode 20 and the geometry of the transmitted diffracted beam FDT at the level of the detection surface of the detector 40.

Naturally, if the second diffractive optical element also had to process the fluorescence, its transfer function would also have to take into account, at the input, the wavelength and geometrical distribution of the fluorescence and, at the output, the geometry of the "beam" of fluorescence transmitted at the level of the interferential filter 35.

The Fourier network is preferable for this second diffractive optical element 42 since, on the one hand, it makes it possible, when it is in centred mode, to limit losses of data to the maximum extent and, on the other hand, by supplying images in a distant field, it makes it possible to directly focus the beams on remote detectors without requiring a convergent lens. Naturally, the engraving of a Fresnel network might be envisaged, but it would then be necessary to couple the second element to a convergent lens.

The relief modulation of the second network is preferably of the type with 16 levels, which makes it possible to obtain a diffraction output of around 95%. An output of this kind is made indispensable by the very low number of diffracted photons, for example.

For material reasons, it is not possible to define exhaustively here, over 1024×1024 points, a diffractive network for example of the Fourier type with two levels of phase. In the absence of this, an image with two levels (black and white) from an example of a diffractive network of this kind is illustrated in FIG. 6.

Although the invention has been described with reference to a device for hematological analyses, it can be used for other comparable applications, with or without fluorescence, which come with the scope of the claims appearing below.

This is the case, for example, with the device which is partially illustrated in FIG. 7 and which constitutes a simplified variant form of the device in FIG. 5. This variant form makes use, once again, of the elements described with reference to FIG. 5, with the exception of those (34–36) which constituted the channel for collecting the fluorescence, of the focusing objective (6) and of the detector (40) for collecting the diffracted light.

The diffracted element 42 focuses, on the detection face of the photodetector 20, the image, in a near field, of the light at the level of the constrained passage 15. In order to achieve this, the diffractive element 42 comprises a diffracting motif of the Fresnel type on its collection face 43. Moreover, because of the elimination of the channel for collecting the fluorescence, the light source 31 (diode) can be installed in the axis of the analysis channel.

The two diffractive elements 32 and 42 can be glued onto the walls of the tank 8. In this case, it is preferable that the diffracting motif 33 of the diffractive element 32 should also be of the Fresnel type. In this way, a device of very low bulkiness, particularly simple construction and reduced cost is produced.

Moreover, modes of embodiment have been described in which the device includes either a single diffractive optical element for shaping the source light, or a diffractive optical element for shaping the source light and a diffractive optical element for collecting the light emanating from the interaction between the fluid and the source light. But other modes of embodiment may naturally be envisaged, such as for example a mode in which use is made only of one (or a number of) diffractive optical element(s) with a view to collecting the light emanating from the interaction between the fluid and the source light.

A mode of embodiment of this kind is illustrated in FIG. 8. It makes use, once again, of the elements described with reference to FIG. 5, with the exception of the diffractive optical element (32), which is replaced by an assembly 50 for collimating the light beam F1 delivered by the light source 31, and by a diaphragm 51 of preferentially rectangular section.

The source 31 is a laser diode, for example, which delivers a beam F1 having an elliptical, divergent section and a Gaussian distribution. The diaphragm 51 selects the central part of the Gaussian distribution in order to ensure homogeneous distribution of the light power delivered at the level of the constrained passage 15.

A device of this kind therefore combines a optical system of the refracting type for shaping the beam, with an optical sub-system of the diffracting type for collecting the light emanating from the interaction between the fluid and the source light.

Other modes of embodiment still may be envisaged, such as for example a mode in which use is made of a diffractive optical element for shaping the source light and of a number of diffractive optical elements with a view to collecting the light emanating from the interaction between the fluid and the source light.

Embodiments of this kind may be useful when the device is intended especially for separating light beams of different wavelengths. In order to accomplish this, it is possible to place the different diffractive elements, which are respectively intended to process a given wavelength, in parallel at the output of a dispersive network or of a dispersion prism, which is itself located at the output of the measuring space (which may be a virtually closed enclosure as in the example described, or else an open zone). Each diffractive optical element then has a three-dimensional motif which is peculiar to it, so that it is able to ensure filtering of the wavelength and/or of the geometrical distribution of the light concerned, and then deliver the light thus filtered to the sensor means concerned, according to the geometrical and spectral characteristics chosen as a function of the said sensor means.

The invention applies generally to devices for the optical inspection of particles of a gaseous or liquid fluid, especially in the fields of flux cytometry, hematology and medical diagnostics.

We claim:

1. Device for the optical inspection of a fluid, of the type which includes:

a measuring space (8) comprising a constrained passage (15) for the fluid, a light source (31), an analysis unit, upstream optical means (6, 32, 34) suitable for collecting the light (F1) emanating from the source (31) and for delivering said collected light (F1) at the level of the constrained passage (15) in the form of an upstream delivered light (FC) having chosen geometrical and spectral characteristics, first sensor means (20) suitable for delivering to said analysis unit (24) first signals which are representative of first data conveyed by a collected light (FT), first downstream optical means (18, 19, 42) for collecting at least part of the light (FT) obtained after passage through the constrained passage (15) and delivering said collected light (FT) from the constrained passage to the first sensor means (20) in the form of a downstream delivered light (FTT, FTD) having chosen geometrical and spectral characteristics, wherein at least one of the upstream optical means (32) and of the first downstream optical means (42) includes at least one first diffractive optical element (32; 42) of which at least one of the surfaces (33; 43), which interact with the light that they collect, has a first predetermined three-dimensional motif which is suitable for carrying out a predetermined interaction between the light that it collects (F1; FT) and the light that it delivers (FC; FTT, FTD).

2. Device according to claim 1, wherein the first diffractive optical element (32) is of the Fresnel type.

3. Device according to claim 1, wherein the first diffractive optical element (32) is of the Fourier type.

4. Device according to claim 1, wherein the geometrical and spectral characteristics chosen, which are required for the illumination of the constrained passage (15), include uniform illumination, at the wavelength chosen, of a substantially plane, closed surface having a given geometry.

5. Device according to claim 4, wherein the illuminated surface is a rectangle.

13

6. Device according to claim 1, wherein the light source (31) is a source having substantially monochromatic radiation, the emission wavelength of which is chosen in such a way that it induces fluorescence of at least part of the fluid passing through the constrained passage (15).

7. Device according to claim 6, wherein it includes second sensor means (36) which are intended to deliver to the analysis unit (24) second signals which are representative of second data conveyed by fluorescence emitted by the fluid at the time of its interaction with the light (FC) at the level of the constrained passage (15).

8. Device according to claim 7, wherein at least one of the diffractive optical elements has a predetermined three-dimensional motif suitable for ensuring filtering of the wavelength and of the geometrical distribution of fluorescence, and for delivering to the second sensor means (36) a fluorescence light having chosen geometrical and spectral characteristics.

9. Device according to claim 1, wherein it includes third sensor means (40) intended to deliver to the analysis unit (24) third signals which are representative of third data conveyed by the light (FTD) diffracted by the fluid at the time of its interaction with the light (FC) at the level of the constrained passage.

10. Device according to claim 9, wherein the first downstream optical means include at least one second diffractive optical element (42), of which at least one of the surfaces (43), which interact with the light (FT) obtained after passage through the constrained passage (15), has a second three-dimensional motif which is predetermined as a function of a frequential and geometrical transfer function of at least one of the first (20) and third (40) sensor means.

11. Device according to claim 10, wherein the second diffractive optical element (42) is of the Fourier type.

12. Device according to claim 10, wherein the second diffractive optical element (42) is of the Fresnel type.

13. Device according to claim 10, wherein the second diffractive optical element includes a single surface (43) comprising a diffracting motif of the Fourier type with sixteen levels.

14. Device according to claim 10, wherein at least one of the diffractive optical elements has a predetermined three-

14 dimensional motif suitable for ensuring spatial separation of predetermined wavelengths.

15. Device according to claim 9, wherein the downstream optical means include the first diffractive optical element (42), of which at least one of the surfaces (43), which interact with the light (F1) delivered by the source (31), has the first three-dimensional motif which is predetermined as a function of a frequential and geometrical transfer function between at least one of the first (20) and third (40) sensor means.

16. Device according to claim 15, wherein the first three-dimensional motif is a first (48) diffractive network engraved in a transparent substrate (49) at the wavelengths of emission of the source and of fluorescence.

17. Device according to claim 1, wherein the upstream optical means include the first diffractive optical element (32), of which at least one of the surfaces (33), which interact with the light (F1) delivered by the source (31), has the first three-dimensional motif which is predetermined as a function of the characteristics of the source (31) and of the chosen characteristics required for the illumination (FC) of the constrained passage (15).

18. Device according to claim 17, wherein the first diffractive optical element (32) includes a single surface (33) comprising a diffracting motif of the Fresnel type with sixteen levels.

19. Device according to claim 17, wherein the first and second three-dimensional motifs are, respectively, first (38) and second (48) diffractive networks engraved in transparent substrates (39; 49) at the emission wavelength of the source and/or the fluorescence wavelength.

20. Device according to claim 19, wherein the first and second diffractive networks (38, 48) are of the digital type with relief modulation, the said modulation representing a predetermined function capable of coherent diffracting action on the phase and/or amplitude, respectively, of the light (F1) emitted by the source (31) and of the light (FT) obtained after passage through the constrained passage (15).

21. Device according to claim 20, wherein the first and second diffractive networks each possess relief modulation of at least two levels.

* * * * *